(12) United States Patent
Rastogi et al.

(10) Patent No.: US 6,469,145 B1
(45) Date of Patent: Oct. 22, 2002

(54) ONE-STEP PURIFICATION PROCESS FOR ORGANOPHOSPHORUS HYDROLASE ENZYME

(75) Inventors: Vipin K. Rastogi, Bel Air, MD (US); Tu-Chen Cheng, Timonium, MD (US); Joseph J. DeFrank, Bel Air, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/603,450

(22) Filed: Jun. 26, 2000

(51) Int. Cl.[7] ............................. C08H 1/00; C07K 1/00; C12P 21/04; C12N 1/20; A61K 38/43
(52) U.S. Cl. ..................... 530/412; 530/350; 530/369; 435/70.1; 435/71.1; 435/69.7; 435/174; 435/252.3; 435/320.1; 424/94.1; 536/23.4
(58) Field of Search ............................. 435/70.1, 71.1, 435/69.7, 252.3, 320.1, 174; 424/94.1; 530/412, 350, 369; 536/23.4

(56) References Cited

U.S. PATENT DOCUMENTS

| | | | | |
|---|---|---|---|---|
| 5,322,930 A | * | 6/1994 | Tarnowski et al. | 530/350 |
| 5,756,311 A | * | 5/1998 | Otto et al. | 435/69.51 |
| 6,010,680 A | * | 1/2000 | Govindan et al. | 424/1.69 |

OTHER PUBLICATIONS

Mulbry et al., "Purification and Characterization of Three Parathion Hydrolases from Gram–Negative Bacterial Strains" Appl. Environ. Microbiol. (Feb. 1989), vol. 55, No. 2, 289–293.

McDaniel et al. "Cloning and Sequency of a Plasmid–Borne Gene opd Encoding a Phosphotriesterase," J. Bacteriol. vol. 170, No. 5, 2306–2311 (1988).

Omburo, et al "Characterization of the Zinc Binding Site of Bacterial Phosphotriesterase", J. Biol. Chem. (1992) vol. 297 No. 19, 13278–13283.

Mulbry et al "Parathion Hydrolase Specified by the Flavobacterium opd Gene: Relationship Between the Gene and Protein", J. Bacteriol. vol. 171, No. 12, 6740–6746.

* cited by examiner

Primary Examiner—W. Gary Jones
Assistant Examiner—Arun Chakrabarti
(74) Attorney, Agent, or Firm—Ulysses John Biffoni

(57) ABSTRACT

Novel and improved processes for isolating organophosphorus hydrolase enzyme from an aqueous solution and obtaining substantially purified enzyme at high yield are provided, as well as compositions, including storage stable lyophilyzed organophosphorus hydrolase enzyme compositions, that are prepared by the provided methods. The organophosphorus hydrolase enzyme is purified by contacting an aqueous solution of cell free bacterial proteins with a strong cation exchange resin, the aqueous solution comprising soluble organophosphorus hydrolase enzyme, washing the strong cation exchange resin with a washing buffer to remove unbound proteins from the strong cation exchange resin, eluting proteins that remain bound to the strong cation exchange resin by washing the resin with an eluting buffer comprising salt in a concentration that starts at about zero and is raised during the eluting process to about 0.5M, and detecting and collecting eluate comprising a protein having organophosphorus hydrolase enzyme activity. All processing steps are conducted at a pH that is less than the isoelectric point of the organophosphorus hydrolase enzyme.

16 Claims, 1 Drawing Sheet

ONE-STEP PURIFICATION PROCESS FOR ORGANOPHOSPHORUS HYDROLASE ENZYME

U.S. GOVERNMENT INTEREST

The invention described herein may be manufactured, used and licensed by or for the U.S. Government for U.S. Government Purposes.

FIELD OF THE INVENTION

The invention relates to an improved and simplified process for purifying organophosphorus hydrolase enzyme ("OPH") from a recombinant host cell, that expresses this enzyme.

BACKGROUND OF THE INVENTION

The threat of exposure to chemical warfare ("CW") agents is of increasing concern for both the armed forces and for civilian populations that might be potentially targeted by terrorists. For this reason, there is an acute need to develop and improve technology for decontamination of CW agents. This is especially true for the class of CW agent known as nerve agents or nerve gases. One class of nerve agents with a high level of potential lethality is the class that includes organophosphorus-based ("OP") compounds, such as Sarin, Soman, and the VX. Such CW nerve agents can be absorbed through inhalation and/or through the skin by the victim. The OP nerve agents typically manifest their lethal effects against animals and people by inhibiting acetylcholine esterase ("AChE") enzyme at neuromuscular junctions between nerve endings and muscle tissue. An excessive buildup of the neurotransmitter, acetylcholine, can result in paralysis and death in a short time.

In addition to the concerns about CW agents, there is also a growing need in industry for decontamination of industrial OP-based insecticides, for example, acetylcholinesterase-inhibiting pesticides such as parathion, paraoxon and malathion, among others. Thus, it is very important to be able to effectively detoxify a broad spectrum of toxic OP compounds on contaminated surfaces and sensitive equipment.

Currently, the U.S. Army uses a nerve agent decontamination solution, DS2, which is composed (by weight) of 2% NaOH, 28% ethylene glycol monomethyl ether, and 70% diethylenetriamine (Richardson, G. A. "Development of a package decontamination system", EACR-1 310-17, U.S. Army Edgewood Arsenal Contract Report (1972), herein incorporated by reference). Although this decontamination solution is effective against OP nerve agents, it is quite toxic, flammable, highly corrosive, and releases toxic by products into the environment. Thus, there is a need for an alternative decontamination technology that is both effective and non-hazardous to personnel, sensitive equipment, and/or the environment.

One potential alternative to DS2 is enzyme-mediated decontamination. Enzymes are biocatalysts that are typically non-toxic, biodegradable, non-corrosive and can be economically produced in the desired quantities. Suitable enzymes are those that effectively catalyze the degradation of OP-based toxic compounds, including CW agents. For example, a class of enzymes known as organophosphorus anhydrolases ("OPAA")(EC 3.1.8.2) can broadly catalyze the hydrolysis of a variety of OP compounds, including fluorinated "G-type" nerve agents. (See, e.g., Landis, W. G., et al., 1987, *J. Appl. Toxicol.* 7:35–41; DeFrank, J. J., et al., 1993, *Chem. Biol. Interact.*, 87: 141–148; both incorporated by reference herein in their entireties). This enzyme, however, does not detoxify V-type CW nerve agents.

Another potentially useful OP-degrading enzymes is organophosphorus hydrolase (OPH; EC 3.1.8.1). OPH is particularly desirable because it is the only well-characterized enzyme that can hydrolyze both United States and Russian Federation types of VX nerve agents. Two common sources for OPH enzyme, to date, are the identical opd genes isolated from *Pseudomonas diminuta* MG and the Flavobacterium sp. strain ATCC 27551. The *P. diminuta* MG opd gene was isolated by McDaniel et al., 1989, *J. Bacteriol.*, 170:2306–2311, incorporated by reference herein in its entirety. The McDaniel et al. opd gene is referenced in Genebank, with ascension number M20392, and incorporated by reference herein in its entirety, as follows.

LOCUS PSEPTE 1322 bp DNA BCT Apr. 21, 1996
DEFINITION Plasmid pCMS1 (from *P. diminuta*) phosphodiesterase (opd) gene, complete cds.
ACCESSION M20392
NID g151517
VERSION M20392.1 GI:151517

The open reading frame of the opd gene, as reported by McDaniel et al., contains 975 bases which encode OPH polypeptide of 325 amino acid residues with a molecular mass of 35 kDa. Mulbry, W. et al., 1989, *J. Bacteriol.*, 171, 6740–6746, incorporated by reference herein in its entirety, also cloned the opd gene, but that clone lacked 4 amino-terminal residues (ser-ile-gly-thr or SIGT), relative to the opd gene described above.

Previously developed procedures for purification of OPH have broadly required four purification steps. See, for example, Omburo, et al., 1992 *J. Biol. Chem.* 267:13278–13283. Omburo, et al., described two precipitation steps and two chromatography steps as listed below:
1. protamine sulfate (0.4%) precipitation and clarification;
2. ammonium sulfate (45%) precipitation with resuspension and dialysis;
3. Ultragel ACA 54™ or Sephacryl S-200™ gel filtration;
4. DEAE-Sephadex A-25™ or DEAE-Sephacel™ ion-exchange chromatography.

Another problem is that the OPH enzyme has a limited shelf-life in aqueous solution, and the previously employed process exposes the OPH enzyme to an aqueous environment for a prolonged time period. For example, at room temperature, the OPH enzyme loses more than 50% of its catalytic performance within 4–5 hours, and the above-described 4-step process requires 4–5 days for completion. Given the number of steps and the prolonged processing times heretofore required, it is clear that this previously employed process has failed to fulfil the need for economical production of OPH enzyme at high yield. In particular, the above-described 4-step process only produces from 1–5 mg of OPH enzyme, per liter of culture. Thus, there remains a longstanding need in the art for improved methods for purifying OPH enzyme to provide the needed quantities for decontamination purposes. In addition, there is also a long-standing need for improved methods for the stable storage of OPH enzyme in order to allow for the stockpiling and transportation of the enzyme to locations requiring decontamination.

SUMMARY OF THE INVENTION

In order to solve these and other problems in the art, the present invention provides the following novel simplified purification processes, as well as a substantially enhanced yield of purified OP-hydrolyzing enzyme by the inventive processes, and other compositions and methods.

Accordingly, the invention provides a process for isolating organophosphorus hydrolase enzyme present in an aqueous solution of cell free bacterial proteins by contacting the aqueous solution of bacterial proteins with a strong cation exchange resin.

The strong cation exchange resin is then washed with a washing buffer to remove unbound proteins. Proteins that remain bound to the strong cation exchange resin are then eluted by washing the resin with an eluting buffer. The eluting buffer is prepared to include salt in a concentration that starts at about zero. The salt concentration of the eluting buffer is raised during the eluting process to about 0.5M, so that bound proteins are driven from the strong cation exchange resin in proportion to the salt concentration gradient.

The inventive process further includes detecting and collecting eluate, e.g., fractions, that include or contain a protein having organophosphorus hydrolase enzyme activity. In the process as exemplified herein, the protein having organophosphorus hydrolase enzyme activity is preferably detected in the eluate in collected fractions ranging in salt concentration from about 0.1 to about 0.2M. Preferably, the salt is NaCl, although any other suitable salt may be readily employed, e.g., any art-known salt that will displace organophosphorus hydrolase enzyme from the strong cation exchange resin without denaturing or deactivating the enzyme, and that is preferably non-toxic, including, simply by way of example, KCl, $CaCl_2$, $MgCl_2$, and the like.

Generally, for optimum storage and stability, the collected eluate is then precipitated with ammonium sulfate at a concentration effective to precipitate OPH, e.g., at about 45%, and then resuspended in a smaller volume of the same buffer, which is then dialyzed to further concentrate the OPH enzyme. The concentrated dialysate is then lyophilized to dryness. Surprisingly, it has been found that storage stability of the dried organophosphorus hydrolase enzyme prepared by the methods of the invention is greatly enhanced when the collected OPH enzyme is lyophilized in the presence of trehalose sugar. Preferably, the trehalose sugar is at a concentration of about 0.25M at the start of the lyophilization process.

The aqueous solution of cell free bacterial proteins is optionally pre-prepared or obtained from a commercial source, or more preferably, is prepared at the same location by cultivating recombinant bacteria, e.g., *Escherichia coli* ("*E. coli*"), that express OPH enzyme in soluble form. The culture is grown to optimal density by art-standard methods, and in a preferred aspect of the invention, the opd gene is under the operable control of an inducible promoter, so that organophosphorus hydrolase enzyme production is induced after a suitable culture density is reached. As exemplified herein, the inducible promoter is a trc promoter. The cultivated recombinant bacteria are harvested, e.g., as a cell paste, and then lysed into a buffered aqueous solution, e.g., by passing the bacteria through a French Cell Press, freeze thawing and/or, ultrasonicating the bacteria Unlysed cells and cellular debris are separated, e.g., by filtration and/or centrifugation to provide an aqueous solution of cell free bacterial proteins.

The invention further provides for a composition that includes a soluble organophosphorus hydrolase enzyme bound to a strong cation exchange resin, such as, for example, Sepharose-SP™ (Amersham Pharmacia Biotech, New Jersey).

DETAILED DESCRIPTION OF THE PREFERRED EMBODIMENTS

Figure 1:
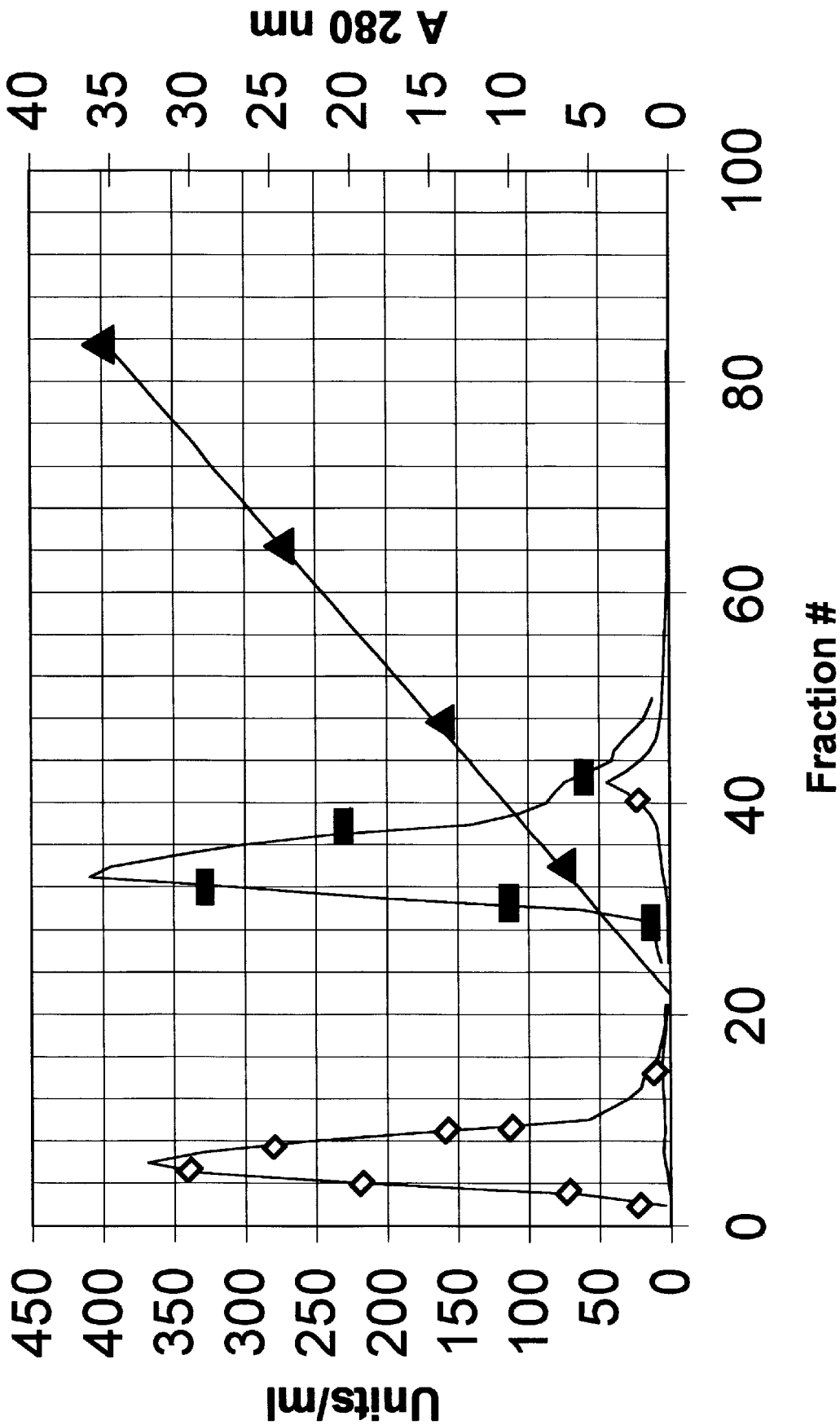
FIG. 1 graphically illustrates ion-exchange chromatography of soluble proteins extracted from recombinant host cells and passed through a Sepharose-SP™ column. The curve marked by diamonds illustrates the total protein washout measured at 280 nm verses collection fraction number. The curve marked by solid rectangles is a separate curve indicating the OPH enzyme activity of fractions associated with the protein curve verses collected fraction number. The curve marked by solid triangles is a separate curve illustrating the rising salt concentration (NaCl) of the elution buffer verses collected fraction number.

The OPH purification process exemplified herein was applied to a soluble OPH enzyme purified from a recombinant clone of *E. coli* containing plasmid pVSEOP7. This clone was constructed using a plasmid designated as pSE420 (Invitrogen Corp., CA, USA), in which a full-length gene encoding soluble OPH enzyme (restricted with Rca I and Pst I) was cloned at NcoI and PstI restriction sites of the plasmid. Thus, the produced OPH differs from the native OPH in being soluble instead of membrane-bound, and in having an initial Met residue. The $Met^1$ substitution for the corresponding native $Ser^1$ does not affect OPH enzyme properties or purification, but is present for the convenience of having a particular useful restriction site at the start of the open reading frame.

In addition, it is also well known in the art that a variety of prokaryotic promoters and host microorganisms are capable of expressing recombinant proteins. Accordingly, it is contemplated that the present invention is not limited to the use of any particular combination of expression vector and host cell for expression of a DNA fragment comprising a DNA sequence coding for soluble OPH. For example, the following expression systems are optionally used to overexpress and purify soluble OPH: pRSET Xpress.™. Kit (Cat. #K880-01, Invitrogen, San Diego, Calif.); pProEX HT™. Protein Expression System (Cat. # 10711-018, Gibco BRL Life Technology, Gaithersburg, Md.); QIAexpress.™. Type VI Kit (Cat. # 32149, Qiagen, Inc., Chatsworth, Calif.); IMPACT™. I System (Cat. # 6500, New England Biolabs, Inc., Beverly, Mass.), to name but a few possible alternatives for soluble OPH expression and production. Details of the preparation of expression vector, with the exemplified trc promoter, and recombinant host cells are provided as follows.

A. Preparation of pVSEOP7

The recombinant strain containing a pJK33 plasmid was graciously provided by Walter Mulbry (U.S. Dept. of Agriculture, Beltsville, Md.) originally prepared as described by Mulbry et al, 1988 Id. supra. pJK33 is a pUC19 derived recombinant plasmid, that contains an opd gene that was originally cloned by Mulbry et al., Id, from Flavobacterium sp. ATCC 27551, as described supra. The cloned gene lacks the first 33 amino-terminal residues of OPH enzyme. Of the 33 missing residues, first 29 of these residues function as signal peptide, rendering the enzyme cell membrane-bound. Removal of the bases encoding the 29 residue signal peptide was intentional, allowing that the enzyme to be produced as a soluble protein. However, removal of the additional four residues, was unintentional. In place of the first four residues (four peptide sequence of serine, isoleucine, glycine, and threonine) of OPH, five residues of beta-galactosidase were present in the mature OPH protein produced by pJK33. Thus, pJK33 produced OPH as a lacz-opd fusion product (Mulbry and Karns, 1989, *Jour. Bacteriol.* 171: 6740–6746). In order to obtain a recombinant expression clone of mature OPH from pJK33, that produces a soluble native-identical OPH, the following alterations were sought:

a. Removal of the unintentional five lacz residues;

b. Restoration of the four native residues, which were serine, isoleucine, glycine, and threonine, in place of the lacz residues; and c. Cloning (in-frame) of full-length opd gene sequence under a high-expression vector.

To incorporate all the above-mentioned alterations, pJK33 plasmid DNA was used as template DNA in a polymerase cycle reaction (PCR) amplification. Two primers were designed with the intention of amplifying a full-length opd gene from pJK33. The 5' or amino-terminal primer was such that it restored the first four residues, but instead of an initial residue of serine, the initial residue was methionine, which provided the advantage of a Rca I restriction site useful for incorporating the OPH coding region the pSE420 expression vector, as detailed below. No significant activity change resulted from the terminal substitution of Met for Ser in the soluble OPH.

As noted above, this amplification also conferred a unique restriction site, Rca I (tca tga, at the 5'-end). The other 3' or carboxy-terminal primer conferred a unique restriction site, PstI (ctg cag, at the 3'-end), producing a vector expressing an OPH having the above-described four missing residues at the amino-terminal end of the OPH. Furthermore, the primers were selected to confer unique restriction sites on the PCR-amplified OPH-encoding gene sequence. The primer sequences were as follows:

5'-ggcgccatttcatgatcgtcggcacaggcgat-3' (SEQ ID NO:1)
 Rca1
 Met-ile-gly-thr- . . .
5'-atccagctgcagtcatgacgcccgcaaggtcgg-3' (SEQ ID NO:2)
 Pst1

PCR amplification was conducted by using thermocycler, GeneAmp PCR System (Perkin Elmer Model 2400). Amplification reactions were carried out in a final volume of 100 ml using 25 cycles of 94° C. (1 min), 50° C. (1 min), 72° C. (1 min), followed by one holding 72° C. (7 min) before holding at 4° C. ( ). Thermostable enzyme Taq polymerase and all the dNTPs were purchased from Perkin Elmer. The resulting PCR-amplified DNA fragment was of ~1,100 bp in length and corresponded in length to the OPH gene encoding the soluble form of native OPH, but with the substitution of an ATG encoding Met for the TCG encoding Ser, as the initial codon, for convenience in positioning the restriction site. Thus, in comparing the CDS expression sequence employed herein to that of SEQ ID NO:3, as published by Mulbry et al., Id., supra, bp 506–508 is now an ATG. The expressed soluble protein has a polypeptide sequence corresponding to SEQ ID NO:4, which indicates the initial Met residue.

The DNA fragment was restricted with Rca I and Pst I restriction enzymes, and ligated to a pSE420 expression vector (Invitrogen Corp., Carlsbad, Calif., USA; catalog # 420-20). Before ligation, the vector was pre-digested with Nco1 and Pst1 restriction enzymes. The sticky ends generated by RcaI enzyme on the OPH gene are complementary to the Nco1 sticky ends of the vector. The resulting recombinant plasmid, pVSEOP7, contained a full-length OPH gene (SEQ ID NO:3), which lacked the five residues of the lacz and encoded the fill-length soluble form of the native OPH enzyme. The expression of the opd gene to produce the OPH was under the control of a trc promoter inducible by isopropyl-beta-D-thiogalactopyranoside ("IPTG"). The trc promoter is a hybrid of the trp promoter and lac operator, as described by Invitrogen product literature accompanying the pSE420 vector. The disclosure of the Invitrogen product literature accompanying the pSE420 vector is incorporated by reference herein in its entirety. Preferably, *E. coli* XL1-Blue™ (available from Stratagene Co., La Jolla, Calif.) is employed. This strain was used in this process to produce OPH enzyme for isolation by the methods of the invention.

B. Simplified Purification Process for OPH Enzyme

The simplified purification of the recombinantly produced OPH enzyme is detailed below. Relative to the previously employed processes (requiring four steps and over four days), discussed supra, in the Background section, the inventive process, as exemplified, employs only a single column purification procedure, and the entire process is accomplished in just over a day (up to about 32 hours). The yields, both relative to starting material and in total weight quantities provided by the inventive processes are also greatly improved relative to the old processes.

1. Culture of Cells for Production of Soluble OPH Enzyme

The processes of the invention are optionally conducted starting with recombinant bacteria expressing OPH enzyme. The OPH enzyme is soluble in the cytosol of the producer strain to facilitate recovery in the aqueous medium and further purification processing. The exemplified OPH expression vector, pVSEOP7, expresses cytosol-soluble OPH and can be transformed into any suitable bacterial host organism, although *E. coli*, is preferred and *E. coli* strain XL1, is exemplified.

The selected XL1 recombinant host organism containing pVSEOP7 was cultured at 28–30° C. in a 6 liter Erlenmeyer culture flask. The autoclaved culture media contained complex Luria-Bertani ("LB") broth (BRL Corp., MD) and also included 100 $\mu$g/ml ampicillin. The culture was shaken @ 180 rpm. The culture was initiated with 1/100th volume of the over-night grown seed culture. When the OD 600 nm reached the range of about 0.5 to about 0.55, the inducer isopropyl-beta-D-thiogalactopyranoside ("IPTG") (Sigma Chem. Co., St. Louis, Mo.) was added at a final concentration of 0.6 mM.

The culture was continued, with shaking, for 14–15 hrs, at which time cobalt chloride at a final concentration of 1 mM was added to the culture. The cells were grown for a further 4–5 hrs, at which time they were harvested.

2. Preparation of Cell-Free Solution Containing Soluble OPH Enzyme

The cells were collected and separated from the culture medium by centrifugation, although any other suitable separation method is readily employed.

The harvested bacteria, in the presence of 20 mM BTP buffer, pH 6.5, buffer (1:4; weight/volume) can be lysed by any art-standard method, including, but not limited to, collecting the harvested culture mass as a wet paste and passaging through a French Cell Press, ultrasonication, enzymatic digestion of the bacterial cell wall in low osmotic solution, freeze thawing, and/or combinations thereof. As exemplified herein, the bacteria were lysed by passaging through a French Cell Press in a buffered aqueous solution.

The unlysed cells and cellular debris are readily separated, by art-standard methods, e.g., by centrifugation, filtration and the like, from the lysing medium, e.g., a buffered aqueous solution, to provide an aqueous solution of cell free bacterial proteins. As exemplified herein, the separation was accomplished by centrifugation.

3. Purification of Soluble OPH Enzyme

The clarified aqueous solution of cell free bacterial proteins is then contacted with any suitable art-known strong cation exchange resin, under conditions that allow binding of soluble OPH to the resin. As exemplified herein, the strong cation exchange resin was Sepharose-SP™ (Amersham Pharmacia Biotech, New Jersey, USA). In an aqueous solution with a pH less than the isoelectric point ("pI"), the OPH enzyme is largely protonated; i.e., it behaves as a cation. The pI of the soluble OPH enzyme is 7.7. Thus, the contacting step is conducted at a pH of less than about 7.7. Preferably, the pH ranges from about 6.2 to about 6.5, e.g., the pH can be about 6.5. The aqueous solution can be any suitable art known buffer including, but not limited to, 10-mM bis-tris propane (BTP) buffer, at pH 6.5.

Once the cell free bacterial proteins have had a chance to bind to the strong cation exchange resin, the resin is then extensively washed, to remove substantially all proteins that remain unbound. Preferably, the wash solutions are monitored for protein content, and the washing continues until the measured protein content is less than 1 microgram of protein per ml, as determined by UV absorbance at 280 nm, calibrated against bovine serum albumin. The wash solution is preferably the same buffer employed for contacting the aqueous solution of cell free bacterial proteins with the strong cation exchange resin.

The bound proteins are then eluted or washed out of the strong cation exchange resin by contacting the strong cation exchange resin with a gradient of buffered salt, e.g., NaCl, ranging in concentration from about zero to about 0.5M, wherein the elution process is conducted at a pH that is less than the isoelectric point of the OPH enzyme, preferably ranging from about 6.2 to about 6.5, e.g., the pH can be about 6.5.

The elution buffer that is collected from the strong cation exchange resin is monitored for protein content (either continuous flow or in discrete collected fractions) and is also optionally monitored for OPH enzyme activity, using a suitable organophosphorus-based substrate, e.g., paraoxon, to determine OPH activity by art-standard methods. For example, as described by McDaniel and Wild, 1988, J. Bacteriol. 170:2306–2311. As confirmed by the Examples below, a single protein peak that corresponds with a peak of OPH activity was obtained from the exemplified recombinant E. coli.

The processes of the invention are readily conducted by any suitable art-standard apparatus for holding the strong cation exchange resin in contact with the buffer solutions, and collecting the eluant and determining protein content and enzyme activity. For small scale preparation, column chromatograph is preferred, as exemplified below. For larger scale purification operations, the described methods are readily adapted to bulk processing equipment, including bulk column chromatography, large-scale processing by mixing resin beads in bulk fluid carriers with carified aqueous solution of cell free bacterial proteins, followed by separation of the beads by settling, filtration and/or centrifugation, or the like, and washing/elution in a resin bed resting on a solution-permeable screen or mesh, and the like.

EXAMPLES

The following examples serve to provide further appreciation of the invention but are not meant in any way to restrict the effective scope of the invention.

Example 1

Purification of Soluble OPH

A. Methods

Purified soluble OPH enzyme was isolated as follows.

E. Coli strain XL1 Blue™ (available from Stratagene) transformed with the pVSEOP7 described supra was cultured in two liters of complex Luria-Bertani (Life Technology/BRL Gaitbersberg Md.) medium, for 18–19 hours at 30° C., as described above. After 18–19 hrs of growth following induction with IPTOG (isopropyl-beta-D-thiogalactopyranoside) inducer to a final concentration of 0.6 mM, to induce the trc promoter enabling expression of the encoded soluble OPH enzyme, the cells were harvested by centrifugation. The spent media was discarded and the cell pellet was suspended in suspension buffer, 10 mM bis-tris propane (BTP), pH 6.5, in a ratio of 4:1 (volume:wet cell wt.). The cell suspension was then passed twice through a French Cell Press (Spectronic Instruments, Rochester, N.Y.) to break the cells. The lysate was then centrifuged @ 18,500×rpm for 60 min in a JA20 rotor using a Beckman centrifuge to rid the sample of unbroken cells and particulate debris.

The resulting cell-free supernatant, comprising an aqueous solution of soluble proteins (~800 mg in a final volume of 50 ml; pH 6.5–6.8) was then passed through a column packed with a strong cation-exchanger SepharoseSP™ (Ameisham Pharmacia Biotech, New Jersey, USA). After loading, the column was washed with 800 ml of the wash buffer (10 mM BTP, pH 6.5) to remove the unbound proteins Seventy-six fractions, each ~10–11-ml, were collected and analyzed for protein content (absorbance @ 280 nm) and OPH activity analysis (paraoxon as substrate). The bulk of the protein (80–90%) failed to bind to the column, and therefore found in this wash fractions. Less than 5% of the OPH activity was detected in the wash fractions.

Following washing, the bound proteins, including those having OPH enzyme activity, were eluted by use of a 0 to 0.5-M sodium chloride gradient in 10-mM BTP buffer, pH 6.5. Ten ml fractions were collected and analyzed for protein content and OPH activity. The bulk of the OPH activity was found to elute between 0. 1 to 0.2M of sodium chloride concentration. These fractions revealed only one major band corresponding in size to OPH, when analyzed on a denaturing sodium dodecyl sulfate-polyacrylamide gel electrophoresis (SDS-PAGE) (not shown).

It should be noted that this column can be reused by regenerating the strong cation resin by first elating all the bound proteins with 300 ml of 2-M sodium chloride equilibrated in 10-mM BTP buffer, pH 6.5. For example, the column can optionally be washed with 0.5 N sodium hydroxide for regenerating the resin, before washing extensively (over 1200 ml) with 10-mM salt-free buffer, before re-use.

B. Results

With reference to FIG. 1, the curves illustrate the exemplified ion-exchange chromatography of soluble proteins extracted from recombinant host cells and passed through a Sepharose-SP™ column.

The curve marked by solid triangles is an independent curve illustrating the rising salt concentration (NaCl) ranging from about 0 to about 0.5M. The salt gradient of the elution buffer is recorded verses collected fraction number (Y axis is inherent).

The curve marked by diamonds illustrates the total protein washout measured at 280 nm, verses collected fraction number (Y axis on right as Absorbance units, calibrated against bovine serum albumin). As indicated by the total protein curve, most of the soluble cellular protein remained unbound to the column and eluted early, in collected fractions 1–16. A smaller peak in the total protein curve, (also diamond labeled) centered on fraction number 41, was bound to the column, and was then eluted as the NaCl gradient in the elution buffer rose from about 0.1 to 0.2M, as indicated by the curve labeled by solid triangles, discussed above. The identity of the protein eluted around fraction number 41 is confirmed to have OPH enzyme activity as illustrated by the separate curve marked by solid rectangles (Y axis on left, measured as enzyme units per ml). Enzyme activity was measured, as described supra, and OPH enzyme activity units are defined as micromoles of substrate hydrolyzed per minute.

C. Yields

With appropriate induction of OPH expression, during growth of the culture, and the simplified purification process of the invention OPH enzyme yields were as follows. Total yields range from about 30 to about 40 mg, or greater, of soluble OPH per liter of culture volume, compared to the yield of from 1–5 mg of OPH/L using previously available culture and purification protocols, as discussed supra. Purity of the soluble OPH enzyme obtained by the inventive methods ranges from about 85 to about 95 percent, or greater, relative to total protein in the final product.

Example 2

Storage as Stable Soluble OPH Enzyme

For long-term storage, the pooled fractions containing OPH enzyme was subjected to ammonium sulfate (Sigma Chemical Co., St. Louis, Mo.) precipitation (45% final concentration). The precipitated proteins were recovered by centrifugation and resuspended in 50 mM TABS buffer, pH 8.5, containing 50 mM cobal chloride. The resuspended protein fraction was transferred into dialysis tubing (GIBCO/BRL-Life technology, Gaithersburg, Md.; 12,000–14,000 molecular weight exclusion limit), that was previously washed thoroughly with distilled water. The protein sample was dialyzed against two liters of the same buffer at 4° C. for 18–24 hrs with one change of the buffer. Dialized protein solution was mixed with trehalose sugar at a conc. of 0.25M, and the mixed solution was lyophilized until all the water content was dried up.

Relative to the aqueous sample of purified OPH, the lyophilized material was found to retain full activity (Table 1). The lyophilized enzyme has been in storage for over 6 months with no apparent loss in its activity.

Table 1

Performance of Lyophilized OPH

| Sample | Specific activity (micro moles/ min/mg protein) | Total units/L broth culture (micromoles/min) |
| --- | --- | --- |
| Aqueous | 71 | 100,673 |
| Lyophilized (+ trehalose) | 107 | 120,030 |

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention. Numerous references are cited in the specification, the disclosures of which are incorporated by reference in their entireties.

What is claimed is:

1. A process for isolating organophosphorus hydrolase enzyme, comprising the steps of:
   (a) cultivating recombinant bacteria that express organophosphorus hydrolase enzyme in soluble form, said bacteria comprising Escherichia coli containing plasmid pVSEOP7;
   (b) lysing said cultivated recombinant bacteria into a buffered aqueous solution and separating out unlysed cells and cellular debris to provide an aqueous solution of cell free bacterial proteins;
   (c) contacting said aqueous solution of cell free bacterial proteins with a strong cation exchange resin, said aqueous solution comprising soluble organophosphorus hydrolase enzyme;
   (d) washing said strong cation exchange resin with a washing buffer to remove unbound proteins from said strong cation exchange resin;
   (e) eluting proteins that remain bound to said strong cation exchange resin by washing said resin with an eluting buffer comprising salt in a concentration that starts at about 0.0 M and is raised during the eluting process to about 0.5 M, and detecting and collecting eluate comprising a protein having organophosphorus hydrolase enzyme activity; and
   wherein steps (c), (d) and (e) are conducted in a single chromatography column at a pH that is less than the isoelectric point of the organophosphorus hydrolase enzyme, and wherein said organophosphorus hydrolase enzyme is recovered in a purity of at least about 90% relative to the total protein in the final product.

2. The process of claim 1, further comprising concentrating the organophosphorus hydrolase enzyme in the collected eluate by treating the eluate with 45% ammonium sulfate to produce a precipitate, resuspending the precipitate in a lesser volume of the eluting buffer, dialyzing the resuspension eluate buffer to further concentrate the organophosphorus hydrolase enzyme, and then lyophilizing the concentrated eluate buffer to dryness.

3. The process of claim 1, wherein eluting step (e) is continued until said eluate removed from contact with said strong cation exchange resin contains less than about 1 micrograms of protein per ml.

4. The process of claim 1, wherein said aqueous buffer has a pH ranging from about 6.4 to about 6.5.

5. The process of claim 1, wherein said washing step (d) is conducted with an aqueous buffer at about pH 6.5.

6. The process of claim 1, wherein a protein peak having organophosphorus hydrolase enzyme activity is detected in said eluate in a range of salt concentration from about 0.1 to about 0.2M.

7. The process of claim 1, wherein said salt comprises NaCl.

8. The process of claim 1, wherein said cell free bacterial protein solution is separated from said unlysed cells and cellular debris by a method selected from the group consisting of centrifugation, filtration, and combinations thereof.

9. The process of claim 1, wherein said bacteria includes an opd gene.

10. The process of claim 9, wherein said opd gene is under the control of an inducible promoter operably connected to said opd gene, and said process further comprises inducing the promoter during cultivation of the bacteria.

11. The process of claim 10, wherein the inducible promoter is a trc promoter.

12. The process of claim 1, wherein said bacteria are lysed by a method selected from the group consisting of passing the bacteria through a French Cell Press, freeze thawing the bacteria, ultrasonicating the bacteria, and combinations thereof.

13. The process of claim 1, wherein said organophosphorus hydrolase enzyme is recovered in a yield ranging of from about 30 to about 40 mg per liter of bacterial culture medium.

14. The process of claim 1, wherein said organophosphorus hydrolase enzyme is recovered in a purity of about 95 percent, relative to total protein in the final product.

15. The process of claim 1, wherein said organophosphorus hydrolase enzyme has a $Met^1$ substitution.

16. The process of claim 2, wherein said lyophilizing step is conducted in the presence of 0.25M trehalose sugar.

* * * * *

SEQUENCE LISTING

<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence:
      Primer

<400> SEQUENCE: 1
ggcgccattt catgatcgtc ggcacaggcg at                                       32

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence:
      Primer

<400> SEQUENCE: 2
atccagctgc agtcatgacg cccgcaaggt cgg                                      33

<210> SEQ ID NO 3
<211> LENGTH: 1693
<212> TYPE: DNA

-continued

```
<213> ORGANISM: Flavobacterium sp
<220> FEATURE:
<221> NAME/KEY: CDS
<222> LOCATION: (506)..(1516)
<223> OTHER INFORMATION: Expresses organophosphorus hydrolase
<221> NAME/KEY: sig_peptide
<222> LOCATION: (419)..(505)
<223> OTHER INFORMATION: Removal of signal peptide allows
      organophosphorus hydrolase to be expressed in soluble form

<400> SEQUENCE: 3
ggatccgagc ggcttaccgg cgccctgctc gaccggttga cccaccatgt ccatatcctc      60
gagatgaacg ggggcagcta tcggcttgcc agcagccgga aacggcaaaa gcacagccac     120
cacgcacagc aagaggaggt gccccccca tgacctgatc agaaaacccc tcatctgctg     180
tgctgaacgg ccttcgctac gctccagacc gttcagcaca gcagatgaaa gcaccgcctc     240
gacaagaggc tttttgttca atccaactgg tacactctta caccggaatc ttgcacaatt     300
ttaccccggc attgacatct gacgcgtcaa cagtaaaaga aacaaccggt tcagatctgc     360
agcctgactc ggcaccagtc gctgcaagca gagtcgtaag caatcgcaag ggggcagcat     420
gcaaacgaga agggttgtgc tcaagtctgc ggccgccgca ggaactctgc tcggcggcct     480
ggctgggtgc gcgagcgtgg ctgga tcg atc ggc aca ggc gat cgg atc aat      532
                              Ser Ile Gly Thr Gly Asp Arg Ile Asn
                                1               5 acc gtg cgc ggt cct atc aca atc tct gaa gcg ggt ttc aca ctg act      580
Thr Val Arg Gly Pro Ile Thr Ile Ser Glu Ala Gly Phe Thr Leu Thr
 10              15                  20                  25 cac gag cac atc tgc ggc agc tcg gca gga ttc ttg cgt gct tgg cca      628
His Glu His Ile Cys Gly Ser Ser Ala Gly Phe Leu Arg Ala Trp Pro
                 30                  35                  40 gag ttc ttc ggt agc cgc aaa gct cta gcg gaa aag gct gtg aga gga      676
Glu Phe Phe Gly Ser Arg Lys Ala Leu Ala Glu Lys Ala Val Arg Gly
             45                  50                  55 ttg cgc cgc gcc aga gcg gct ggc gtg cga acg att gtc gat gtg tcg      724
Leu Arg Arg Ala Arg Ala Ala Gly Val Arg Thr Ile Val Asp Val Ser
         60                  65                  70 act ttc gat atc ggt cgc gac gtc agt tta ttg gcc gag gtt tcg cgg      772
Thr Phe Asp Ile Gly Arg Asp Val Ser Leu Leu Ala Glu Val Ser Arg
     75                  80                  85 gct gcc gac gtt cat atc gtg gcg gcg acc ggc ttg tgg ttc gac ccg      820
Ala Ala Asp Val His Ile Val Ala Ala Thr Gly Leu Trp Phe Asp Pro
 90                  95                 100                 105 cca ctt tcg atg cga ttg agg agt gta gag gaa ctc aca cag ttc ttc      868
Pro Leu Ser Met Arg Leu Arg Ser Val Glu Glu Leu Thr Gln Phe Phe
                110                 115                 120 ctg cgt gag att caa tat ggc atc gaa gac acc gga att agg gcg ggc      916
Leu Arg Glu Ile Gln Tyr Gly Ile Glu Asp Thr Gly Ile Arg Ala Gly
            125                 130                 135 att atc aag gtc gcg acc aca ggc aag gcg acc ccc ttt cag gag tta      964
Ile Ile Lys Val Ala Thr Thr Gly Lys Ala Thr Pro Phe Gln Glu Leu
        140                 145                 150 gtg tta aag gcg gcc gcc cgg gcc agc ttg gcc acc ggt gtt ccg gta     1012
Val Leu Lys Ala Ala Ala Arg Ala Ser Leu Ala Thr Gly Val Pro Val
    155                 160                 165 acc act cac acg gca gca agt cag cgc gat ggt gag cag cag gcc gcc     1060
Thr Thr His Thr Ala Ala Ser Gln Arg Asp Gly Glu Gln Gln Ala Ala
170                 175                 180                 185 att ttt gag tcc gaa ggc ttg agc ccc tca cgg gtt tgt att ggt cac     1108
Ile Phe Glu Ser Glu Gly Leu Ser Pro Ser Arg Val Cys Ile Gly His
                190                 195                 200
```

-continued

```
agc gat gat act gac gat ttg agc tat ctc acc gcc ctc gct gcg cgc      1156
Ser Asp Asp Thr Asp Asp Leu Ser Tyr Leu Thr Ala Leu Ala Ala Arg
            205                 210                 215 gga tac ctc atc ggt cta gac cac atc ccg cac agt gcg att ggt cta      1204
Gly Tyr Leu Ile Gly Leu Asp His Ile Pro His Ser Ala Ile Gly Leu
        220                 225                 230 gaa gat aat gcg agt gca tca gcc ctc ctg ggc atc cgt tcg tgg caa      1252
Glu Asp Asn Ala Ser Ala Ser Ala Leu Leu Gly Ile Arg Ser Trp Gln
    235                 240                 245 aca cgg gct ctc ttg atc aag gcg ctc atc gac caa ggc tac atg aaa      1300
Thr Arg Ala Leu Leu Ile Lys Ala Leu Ile Asp Gln Gly Tyr Met Lys
250                 255                 260                 265 caa atc ctc gtt tcg aat gac tgg ctg ttc ggg ttt tcg agc tat gtc      1348
Gln Ile Leu Val Ser Asn Asp Trp Leu Phe Gly Phe Ser Ser Tyr Val
                270                 275                 280 acc aac atc atg gac gtg atg gat cgc gtg aac ccc gac ggg atg gcc      1396
Thr Asn Ile Met Asp Val Met Asp Arg Val Asn Pro Asp Gly Met Ala
            285                 290                 295 ttc att cca ctg aga gtg atc cca ttc cta cga gag aag ggc gtc cca      1444
Phe Ile Pro Leu Arg Val Ile Pro Phe Leu Arg Glu Lys Gly Val Pro
        300                 305                 310 cag gaa acg ctg gca ggc atc act gtg act aac ccg gcg cgg ttc ttg      1492
Gln Glu Thr Leu Ala Gly Ile Thr Val Thr Asn Pro Ala Arg Phe Leu
    315                 320                 325 tca ccg acc ttg cgg gcg tca tga cgccatctgg atccttccag ccagcggcca    1546
Ser Pro Thr Leu Arg Ala Ser
330                 335 ctattcccg tcaagatacc gaacgatgaa gtcgcgcatc gatcgatagg catcttcaat    1606
ttgatcaggg ctgccacctc caaagccgtg gccacccctg tcgatagtct tgaggacgta   1666
gggcacaccg tgcttttcga actgcag                                       1693

<210> SEQ ID NO 4
<211> LENGTH: 336
<212> TYPE: PRT
<213> ORGANISM: Flavobacterium sp

<400> SEQUENCE: 4

Met Ile Gly Thr Gly Asp Arg Ile Asn Thr Val Arg Gly Pro Ile Thr
1               5                   10                  15

Ile Ser Glu Ala Gly Phe Thr Leu Thr His Glu His Ile Cys Gly Ser
            20                  25                  30

Ser Ala Gly Phe Leu Arg Ala Trp Pro Glu Phe Phe Gly Ser Arg Lys
        35                  40                  45

Ala Leu Ala Glu Lys Ala Val Arg Gly Leu Arg Arg Ala Arg Ala Ala
    50                  55                  60

Gly Val Arg Thr Ile Val Asp Val Ser Thr Phe Asp Ile Gly Arg Asp
65                  70                  75                  80

Val Ser Leu Leu Ala Glu Val Ser Arg Ala Ala Asp Val His Ile Val
                85                  90                  95

Ala Ala Thr Gly Leu Trp Phe Asp Pro Pro Leu Ser Met Arg Leu Arg
            100                 105                 110

Ser Val Glu Glu Leu Thr Gln Phe Phe Leu Arg Glu Ile Gln Tyr Gly
        115                 120                 125

Ile Glu Asp Thr Gly Ile Arg Ala Gly Ile Ile Lys Val Ala Thr Thr
    130                 135                 140

Gly Lys Ala Thr Pro Phe Gln Glu Leu Val Leu Lys Ala Ala Ala Arg
```

-continued

```
145                 150                 155                 160
Ala Ser Leu Ala Thr Gly Val Pro Val Thr Thr His Thr Ala Ala Ser
                165                 170                 175

Gln Arg Asp Gly Glu Gln Gln Ala Ala Ile Phe Glu Ser Glu Gly Leu
                180                 185                 190

Ser Pro Ser Arg Val Cys Ile Gly His Ser Asp Asp Thr Asp Asp Leu
                195                 200                 205

Ser Tyr Leu Thr Ala Leu Ala Ala Arg Gly Tyr Leu Ile Gly Leu Asp
            210                 215                 220

His Ile Pro His Ser Ala Ile Gly Leu Glu Asp Asn Ala Ser Ala Ser
225                 230                 235                 240

Ala Leu Leu Gly Ile Arg Ser Trp Gln Thr Arg Ala Leu Leu Ile Lys
                245                 250                 255

Ala Leu Ile Asp Gln Gly Tyr Met Lys Gln Ile Leu Val Ser Asn Asp
                260                 265                 270

Trp Leu Phe Gly Phe Ser Ser Tyr Val Thr Asn Ile Met Asp Val Met
            275                 280                 285

Asp Arg Val Asn Pro Asp Gly Met Ala Phe Ile Pro Leu Arg Val Ile
        290                 295                 300

Pro Phe Leu Arg Glu Lys Gly Val Pro Gln Glu Thr Leu Ala Gly Ile
305                 310                 315                 320

Thr Val Thr Asn Pro Ala Arg Phe Leu Ser Pro Thr Leu Arg Ala Ser
                325                 330                 335
```